(12) United States Patent
Ertl et al.

(10) Patent No.: US 6,692,502 B1
(45) Date of Patent: *Feb. 17, 2004

(54) PROCESS AND INSTRUMENTATION FOR ARTHROSCOPIC REDUCTION OF CENTRAL AND PERIPHERAL DEPRESSION FRACTURES

(76) Inventors: Janos Paul Ertl, 4824 Oak Vista Dr., Carmichael, CA (US) 95608; Joseph John Spranza, III, 808 Tiffany Way, Dallas, TX (US) 75218

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/669,132

(22) Filed: Jun. 24, 1996

(51) Int. Cl.[7] .................................................. A61B 17/56
(52) U.S. Cl. ............................ 606/86; 606/190; 604/60
(58) Field of Search ............................. 606/53, 57, 86, 606/88, 89, 90, 92, 93, 94, 95, 105, 84; 623/16; 604/57–64

(56) References Cited

U.S. PATENT DOCUMENTS

| | | | | |
|---|---|---|---|---|
| 2,543,780 A | * | 6/1951 | Hipps et al. | 606/86 |
| 2,647,512 A | * | 8/1953 | Johnson | 604/64 |
| 4,659,326 A | * | 4/1987 | Johnson et al. | 604/62 |
| 4,790,819 A | * | 12/1988 | Li et al. | |
| 5,071,410 A | * | 12/1991 | Pazell | |
| 5,217,463 A | * | 6/1993 | Mikhail | 606/86 |
| 5,325,883 A | * | 7/1994 | Orr | |
| 5,352,219 A | * | 10/1994 | Reddy | |
| 5,405,324 A | * | 4/1995 | Wiegerinck | 604/59 |
| 5,591,232 A | * | 1/1997 | Rahimi et al. | 606/86 |

* cited by examiner

Primary Examiner—David O. Reip

(57) ABSTRACT

A process with special instruments to Arthroscopically reduce certain joint fractures in humans and animals. The instruments are shaped and sized so as to afford remote manipulation of bone fragments, while viewing the procedure with an arthroscope and a fluoroscope in a C Arm. The process utilizes a lateral approach. This process with the instruments allows a skilled surgeon to affect an anatomically correct joint surface and then bone graft any bone deficit, all through small incisions local to the joint.

5 Claims, 4 Drawing Sheets

PROCESS AND INSTRUMENTATION FOR ARTHROSCOPIC REDUCTION OF CENTRAL AND PERIPHERAL DEPRESSION FRACTURES

BACKGROUND

1. Field of Invention

This invention relates to surgical processes and instrumentation for the repair of a specific type of fracture found in human and animal joints.

2. Discussion of Prior Art

In the field of Orthopaedic surgery, patients frequently present with serious depression fractures of the articulating surfaces in joints. Such trauma is relatively common in the articulating surfaces of the femoral condyles and the tibial plateau. These fractures result from overloading the joint surfaces during falls, automobile accidents, sports play and other high impact situations. The extreme pressures of the impact actually overload the strength of the joint articulating surfaces, causing one joint surface to be driven into the other joint surface; commonly the rounded condyles into the more planar surfaces of the tibial plateau. Here-to-fore, surgeons needed to incise the joint wide open to repair such depression fractures. Even though it has been widely known and accepted to do joint repairs with a minimum of invasion, there was no technique available which was reduced to the combination of a process and a set of specially designed instruments.

Mention of the desirability of an Arthroscopic procedure for reducing depression fractures is found in the medical book "Orthopaedic Trauma Protocols" Eds. Sigvard T. Hansen, Jr. and Marc F. Swiontkowski both of Harborview Medical Center; Publisher, Raven Press, Ltd., New York, N.Y. An additional publication, *Technique for Arthroscopic Fracture Management System*, a commercial advertising flyer put out in 1995 by Acufex Microsurgical Inc., suggests that using a device called an "intra-articular guide" (which is sold by Acufex Microsurgical, and was designed for other procedures) will aid surgeons to reduce intra-articular fragments. This literature does not suggest instruments for remotely manipulating bone fragments, nor does it speak to a process for adjusting the level of the articular surface to make it anatomically correct.

Nowhere in the literature is there mention of a cohesive procedure and/or set of instruments for actually performing an Arthroscopic reduction of an articular depression fracture. Further, nowhere is there the suggestion that a depression fracture may be reduced arthroscopically by a lateral approach.

OBJECTS AND ADVANTAGES

Accordingly, several objects and advantages of our invention are:

The object of this invention is to provide a process and the required instruments to enable a surgeon to repair depression fractures through an incision only 1 to 2 cm long. This is an Arthroscopic procedure with a minimum of invasion. In addition to the 1 to 2 cm incision in the above sentence, there are typically two more incisions (standard Arthroscopic portals) ½ cm long; the second one for the arthroscope and the third for irrigation.

The combined procedure and hardware of this invention allows a skilled surgeon to accomplish an Arthroscopic reduction of an articular surface depression fracture in a joint, with only limited incisions, using a lateral approach. This procedure and instrument system allow a surgeon to affect a reduction of depression fractures, especially those of the central and peripheral tibial plateaus, without opening wide the knee. Further, this technique does not require soft tissue stripping.

The same above mentioned incisions are used again when bone grafting any bone deficit. All necessary bone grafting is performed using the procedure and two of the instruments of this invention.

This procedure and instrument system further allows a surgeon to fixate a loose body fracture fragment. Only one 1 to 2 cm incision and the usual Arthroscopic portals are required, that is, the procedure is performed arthroscopically. Previous surgical techniques required a very extensive incision; opening the entire knee.

This invention saves time. It requires much less time to open and close a 1 to 2 cm incision than a 25 cm incision.

This invention saves trauma. Much less damage is done to soft tissue; muscles and tendons and ligaments need not be resected. This surgery has very minimal invasion. Previous surgical techniques required much greater invasion. Increased scarring and devascularization are associated with extensive invasion.

This invention reduces rehabilitation time. The standard incision, such as cutting a knee wide open, requires that all of the affected tissues be dissected or split. Rehabilitation then requires that all of the affected tissue heal and revascularize. This healing, growing back, is time consuming. The patient is uncomfortable and out of the work force.

This invention may reduce future joint problems. It is widely known that articular surface irregularities lead to early arthritis. In the medical community it is well known and accepted that Arthroscopic surgery is less traumatic to the patient than major invasive open surgery. Less trauma means that there is less rehabilitation.

Further objects and advantages of our invention will become apparent from a consideration of the drawings and ensuing description.

LIST OF REFERENCE NUMERALS

1. Disimpacter
2. Regular Metaphyseal reduction Instrument
3. Great Curvature Metaphyseal Reduction Instrument
4. Curved Dome Metaphyseal Reduction Instrument
5. Intra-articular Counter Reduction Instrument
6. Bone Graft Impacter
7. Bone Graft Reservoir
7a. Bone Graft Reservoir with Impacter inserted
8. Probe
9. Handle 10. Planar surface of instruments #2 and 3, diamond grooved 11. Hemispherical surface of instrument #4, diamond grooved

SUMMARY OF THE INVENTION

The invention of this specification is the combination of a process and the required instruments to arthroscopically reduce a depression fracture of an articulating surface in a human or animal joint. Specifically, this invention allows a surgeon to reduce depression fractures of the central and peripheral tibial plateau, with a minimum of invasion and trauma. The surgery is Arthroscopic, performed through a 1 to 2 cm incision and several standard ½ cm Arthroscopic portals.

DESCRIPTION AND OPERATION OF INVENTION

Figure 1:
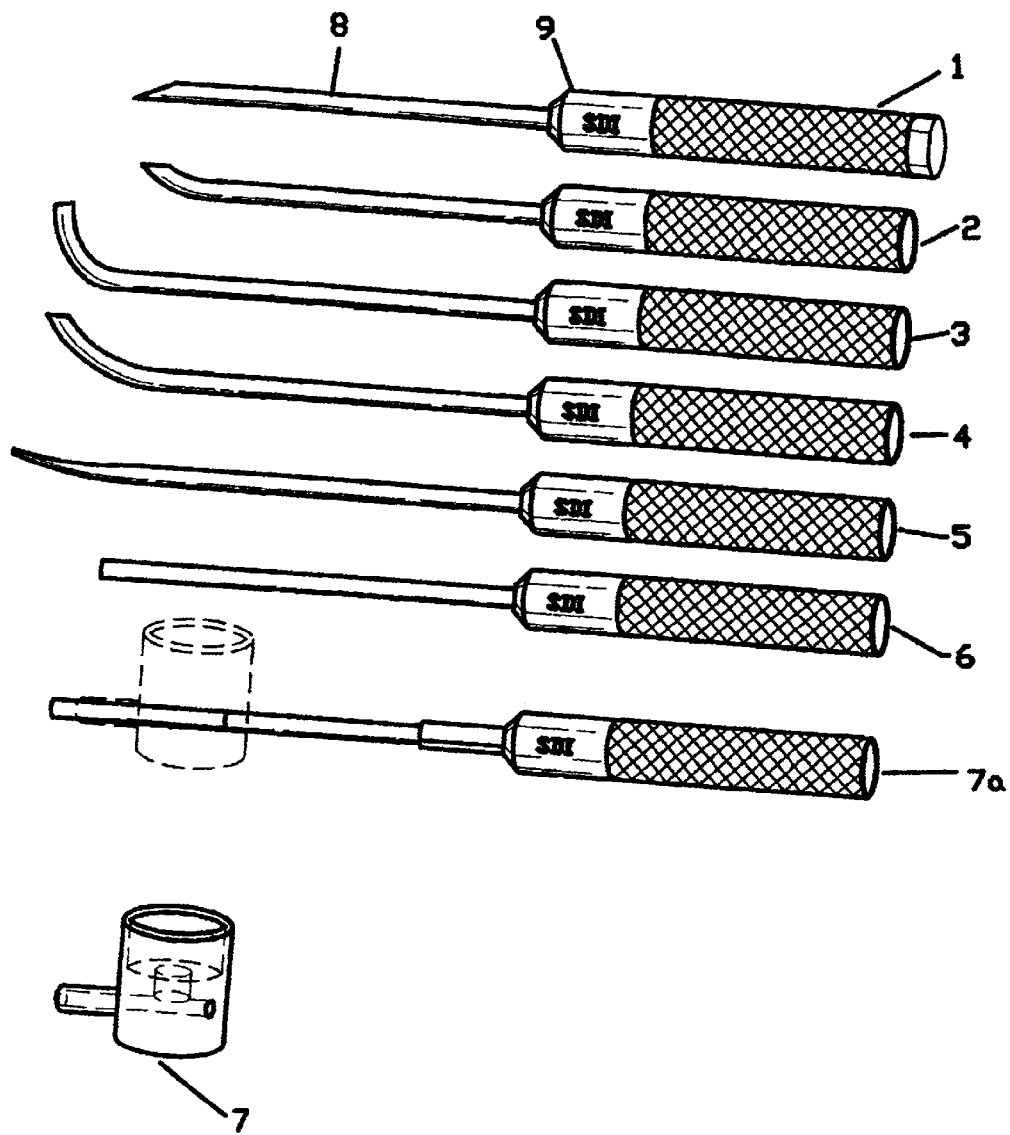
FIG. 1 is a perspective drawing of the seven instrument set of this invention.

FIG. 1 shows a perspective view of the instrument set used to affect the process of this invention. The instruments, numbers 1 through 5 have rod-like probes, #8, attached to handles, #9. The probes are sufficiently long to reach from outside the skin of the patient, to the depths of the damaged joint. Each probe is shaped to enable access to the joint inner anatomy. The terminal tip of each probe is shaped to perform a particular task.

Figure 2:
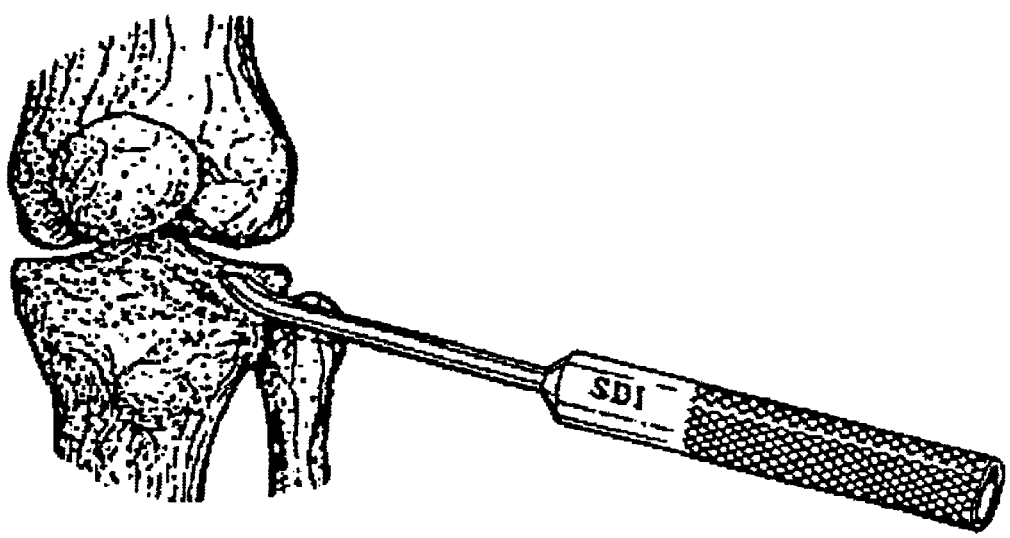
FIG. 2 shows instrument #2, the regular metaphyseal reduction instrument, pushing up a depressed central tibial plateau articular surface.
Figure 4:
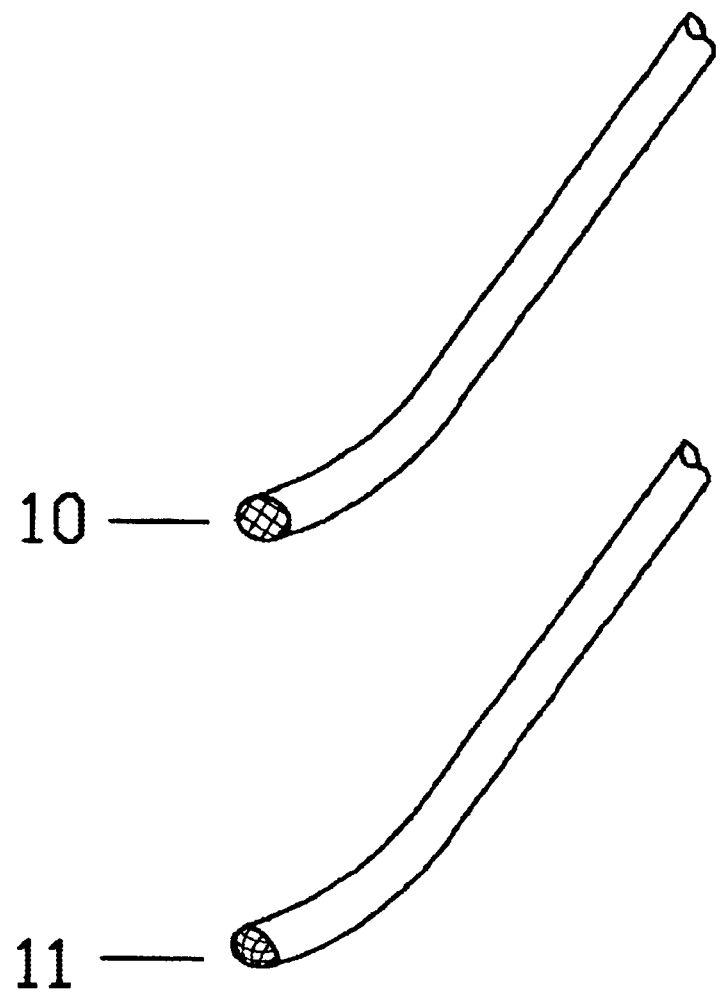
FIG. 4 shows details of the ends of the probes in instruments #'s 2, 3 and 4.

To do an Arthroscopic reduction of a central or peripheral depression fracture of the tibial plateau, utilizing a lateral approach, make a 1 to 2 cm incision anterior and lateral to the fibular head. Using the C Arm for fluoroscopic observation, drill a 4.5 mm diameter hole through the lateral cortex of the tibia, at the approximate level of the epiphysis. This hole should be inferior to or at the level of the bone fragments which are resulting from the depression fracture. The purpose of this 4.5 mm hole is to afford access to the base of the fracture. Push instrument #1, the disimpacter, into the 4.5 mm hole, along the axis of the hole. (See FIG. 2.) The disimpacter has a rod shaped probe which has a flat end to push the bone. This flat end is angled relative to the axis of said probe. Work with the angular face of the instrument directed toward the desired final position of the bone fragments. As you manipulate, observing with the aid of the C Arm fluoroscope and arthroscope, gently force the compressed, depressed bone fragments up to the proper level (the anatomically correct level). This maneuver will create a void in the bone, when the instrument is removed. Observe the articular surface which was depressed by the extreme forces of the accident. It is now necessary to level any area and make it anatomically correct, as before the fracture. Refer to FIG. 1. Instruments numbers 2, 3, and 4 have curved probes. The probes terminate in faces shaped specifically to enable the user to access and manipulate the bone stock upward from beneath the articulating surface. Refer to FIG. 4, #'s 10 and 11. The faces of the probes of instruments 2 and 3 are planar and are angled relative to the axis of curvature. These faces are further grooved in a "diamond" pattern to enhance manipulation of bone fragments. See FIG. 4. Select from these instruments the one or more which provide access to the region beneath the tibial plateau where it must be manipulated. For a more proximal region, select instrument #2. For a rather more distal region, select instrument #4. Instrument #3 may be used for intermediate regions. Note again that each of the instruments has an end which is textured and treated to facilitate the remote manipulation of bone fragments. Instrument #4 has a probe of a substantially long radius. Said probe is terminated in a hemisphere. FIG. 4, #11. The surface of this rounded end is grooved in a "diamond" pattern. Instrument #5, the intra-articular counter reduction instrument, is used to smooth out the articular surface. The probe of instrument #5 is rod shaped, with the distal portion of the rod shaped to a flattened curve. Said shape facilitates smoothing of the damaged articular surface to an anatomically correct shape. To use this instrument, enter it into a hole above the articular surface, in the joint space. One of the two holes in the joint space which are used for irrigation and arthroscoping may be used for this process. Observing with the aid of the arthroscope and the fluoroscope of the C Arm, smooth down the freshly pushed up articular surface so that it is anatomically correct. It may be necessary to simultaneously push up from beneath the fracture with either instrument #2 and or 3 and or 4 as you smooth down the articular surface with instrument #5. It may also be necessary to re-attach (fixate) a bone fragment with a fastener (bone screw). When the surface is anatomically correct, withdraw the instruments. At this time, there will be a void in the bone (a bone deficit). This void will be filled by performing a bone graft.

Figure 3:
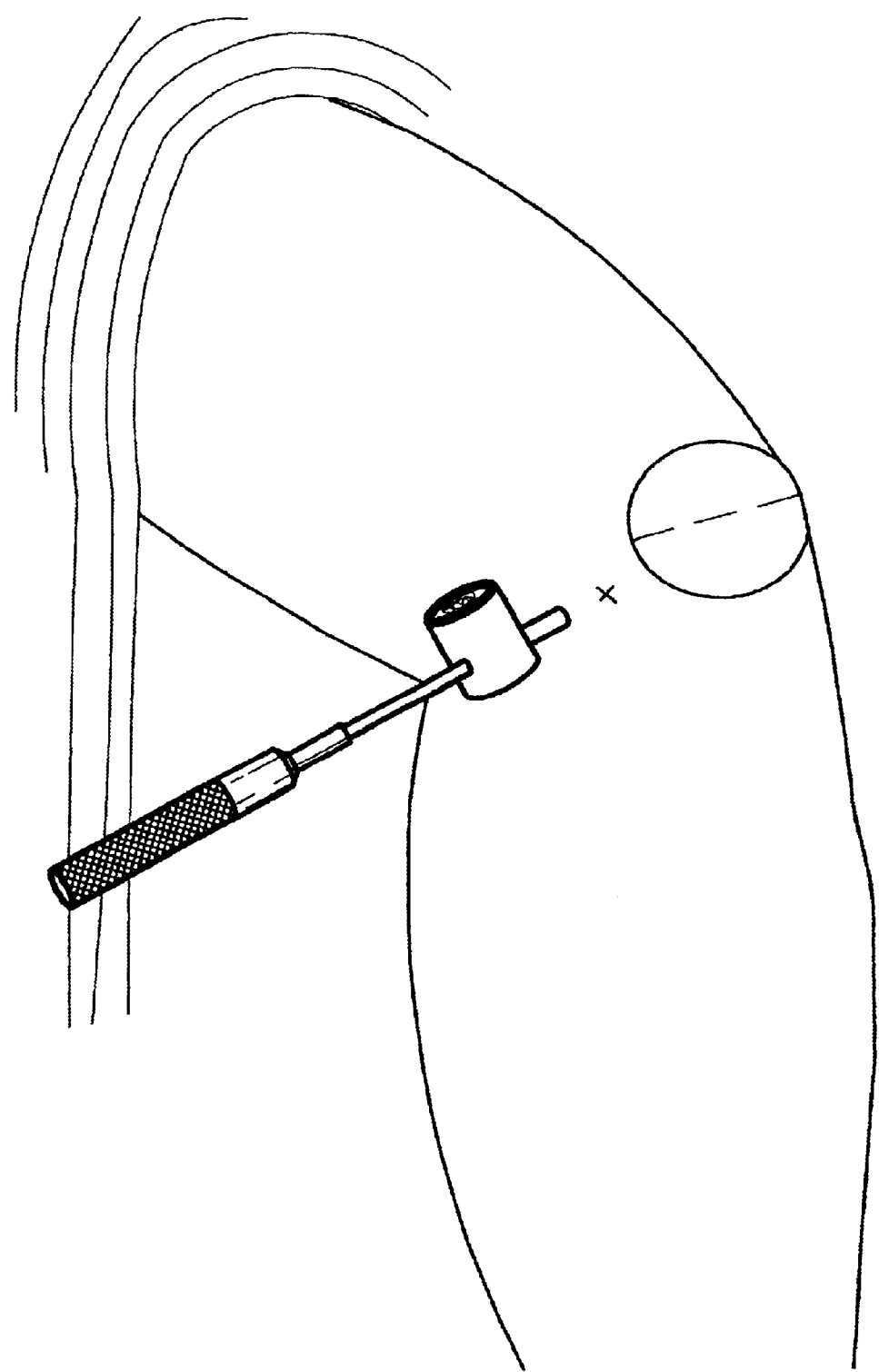
FIG. 3 shows instrument #7, the bone graft reservoir with impacter, inserted into the lateral supra-fibular incision in the knee, described in this process.

Prepare a quantity of morselized bone material to use in a bone graft. Place this bone grafting material into the bowl of the bone graft reservoir cup, instrument #7, FIG. 1. Insert the small tube of the bone graft reservoir cup into the 4.5 mm hole in the tibia. Refer to FIG. 3. Push the bone graft impacter, instrument #6, into the small hole in the bone graft reservoir cup, see FIG. 1, # 7a. A hole in the bottom of the cup communicates with a lateral hole in the cup into which the bone graft impacter has been entered. Bone graft material settles down said communicating hole into this lateral hole, and the bone graft impacter then pushes the bone material through the tube into the hole and ultimately into the bone deficit in the subject tibia. Having pumped the appropriate quantity of morselized bone material into the bone deficit, remove the bone reservoir. The fresh bone graft may require fixation by a bone screw and small plate or washer. If there is a loose bone fragment which requires fixation, it is possible to use the same fastener for both the loose body and for covering the hole into which the bone graft was pumped.

CONCLUSIONS, RAMIFICATIONS, AND SCOPE OF INVENTION

Thus, the reader will see that this invention, the process and instrumentation for Arthroscopically reducing central and peripheral depression fractures of the joints, provides the surgeon both the tools and method for cutting surgical time, reducing trauma, and enhancing recovery. Arthroscopy is widely accepted today as a valuable new technique in surgery. The process and hardware of this invention is a breakthrough in joint surgery.

While our above description contains many specificities, these should not be construed as limitations on the scope of the invention, but rather as an exemplification of one preferred embodiment thereof. Many other variations are possible. For example, the curves of the instruments may vary in radius, as may the angles. The diameter of the individual probes may be smaller or larger. The number of instruments may vary so as to include compound angles, compound curves for ease of access. There may be fewer instruments. The materials may vary, to include other metals, and even plastics. A probe may be articulated so as to afford bone manipulation telemanually. The bone graft reservoir may include a grinder, to particulate the bone. The instruments may be of use in approaches other than lateral. The process and instruments may be used in joints other than tibial/femoral.

Accordingly, the scope of the invention should be determined not by the embodiment(s) illustrated, but by the appended claims and their legal equivalents.

We claim:

1. In the area of surgery, an arthroscopic fracture reduction kit for the percutaneous reduction of depression fractures, comprising:
   a. a plurality of probes, each probe having a structural configuration for performing a respective percutaneous fracture reduction procedure, and
   b. means for pumping bone graft, said pumping means further including,
   means for accessing a bone void, and wherein,
   a selected one of said plurality of probes is further designed to advance bone graft through said accessing means of said pumping means.

2. The kit of claim 1, wherein the plurality of probes comprises at least 6 probes, comprising:
   a first probe of substantially linear dimensions having an acutely angled flat face, said face having a textured surface, for disimpaction of depressed bone fragments from limb bones,
   a second probe of substantially linear dimensions having a curve of first radius through a substantially small angle at a distal end, said curve terminating in a flat face, said face being co-planar with a linear axis of said probe and having a textured surface, for reduction of depressed fragments from metaphyseal bone,
   a third probe of substantially linear dimensions having a curve of first radius through a substantially large angle at a distal end, said curve terminating in a flat face, said face being co-planar with a linear axis of said probe and having a textured surface, for reduction of depressed fragments from deeper metaphyseal bone,
   a fourth probe of substantially linear dimensions having a curve of second radius longer than first radius, through a substantially small angle at a distal end, said curve terminating in a hemispherical face, said face having a textured surface, for anatomic correction of reduced fragments from metaphyseal bone,
   a fifth probe of substantially linear dimensions having a curve of said second radius of curvature through a substantially small angle at a distal end, said curve terminating in a spatulate shape, for anatomic counter reduction of fragments in the articular surface,
   a sixth probe of substantially linear dimensions, terminating in a concave face perpendicular to a linear axis of said linear dimensions, for advancing bone graft into a bone deficit,
   wherein each of said probes is uniquely configured such that by selecting an appropriate configuration from the probe characteristics of length, face shape, face texture, and curve radius, a surgeon may percutaneously manipulate bone and cartilage fragments for reduction of depression fractures and anatomically level articular surface in bone joints.

3. The kit of claim 2, wherein the pumping means comprises:
   a main body comprising:
      a first end open to a large inner volume, and
      a second end closed to said large inner volume, and
      a first side having a guide receiver means, and
      a second side having a delivery means for delivering bone graft into a bone void, and
      a connection means between said guide receiver means and said delivery means, and
      a conduit means between said large inner volume and said connection means, and
      a third and a forth side for manipulation of said main body, and
   a selected one of said plurality of probes further designed to enter guide means and pass to and through said delivery means to a bone deficit wherein,
   bone graft material may be deposited through said first open end into said large inner volume and advance through said conduit means into said connection means, and further wherein,
   said bone graft material may be advanced by said probe through said delivery means into a bone deficit.

4. In the area of surgery, a method for percutaneously reducing depression fractures in a joint space, comprising the steps of,
   providing an arthroscopic fracture reduction kit having a plurality of probes, each probe having a structural configuration for performing a respective percutaneous fracture reduction procedure, and
   means for pumping bone graft, said pumping means further including,
      a. means for accessing a bone void, and wherein,
      b. a selected one of said plurality of probes is further designed to advance bone graft through said accessing means of said pumping means.
   percutaneously drilling a hole inferior and latero-anterior through the cortex into a bone space beneath a depression fracture of a tibia plateau, said hole being an access hole,
   entering a first probe of substantially linear dimensions having an acutely angled flat face, said face having a textured surface, into said access hole and advancing said first probe inward and upward so as to disimpact compressed bone fragments and move these fragments so as to partially reduce the depression fracture, withdrawing the first probe and,
   entering a second probe of substantially linear dimensions having a curve of first radius through a substantially small angle at a distal end, said curve terminating in a flat face, said face being co-planar with a linear axis of said probe and having a textured surface, through the access hole and advancing said second probe inward and upward so as to manipulate bone fragments from the metaphysis and further reduce the depression fracture, and withdrawing the second probe and,
   entering a third probe of substantially linear dimensions and having a curve of first, radius through a substantially large angle at a distal end, said curve of first radius terminating in a flat face, said face being co-planar with a linear axis of said probe and having a textured surface, through the access hole and advancing said third probe inward and upward so as to manipulate bone fragments from the metaphysis and yet further reduce the depression fracture, and withdrawing the third probe and,
   entering a fourth probe of substantially linear dimensions and a curve of second radius longer than said first radius, through a substantially small angle at a distal end, said curve of second radius terminating in a hemispherical face, said face having a textured surface, through the access hole and advancing said fourth probe inward and upward so as to manipulate bone fragments from the metaphysis and yet further reduce the depression fracture, and withdrawing the fourth probe and, entering in the joint space, a fifth probe of substantially linear dimensions having a curve of said second radius through a substantially small angle at a distal end, said curve of said second radius terminating in a spatulate shape, and advancing said fifth probe and manipulating articular bone fragments to affect an anatomic reduction of the depression fracture in the joint space, and entering means for accessing the bone void into the access hole, charging said means with bone graft material and, selecting a sixth probe of substantially linear dimensions, terminating in a concave face perpendicular to a linear axis of said substantially linear dimension, and advancing said bone graft material into any bone void created by manipulating bone fragments and reducing the fracture, and alternately advancing the fifth probe and manipulating articular bone fragments to affect an anatomic reduction of the depression fracture, and advancing further bone graft material into any bone void so as to affect percutaneously an anatomic reduction of the depression fracture.

5. In the area of surgery, a method for percutaneously reducing depression fractures in a joint space, comprising the steps of, providing an arthroscopic fracture reduction kit having a plurality of probes, each probe having a structural configuration for performing a respective percutaneous fracture reduction procedure, and means for pumping bone graft, said pumping means further including, a. means for accessing a bone void, and wherein, b. a selected one of said plurality of probes is further designed to advance bone graft through said accessing means of said pumping means, percutaneously drilling a hole inferior and latero-anterior through the cortex into a bone space beneath a depression fracture of a tibia plateau, said hole being an access hole, entering a first probe of substantially linear dimensions having an acutely angled flat face, said face having a textured surface, into said access hole and advancing said first probe inward and upward so as to disimpact compressed bone fragments and move these fragments so as to partially reduce the depression, withdrawing the first probe and selecting between the remaining instruments a second probe, and entering said second probe into the access hole and advancing said second probe inward and upward so as to manipulate bone fragments from the metaphysis and further reduce the depression fracture, and withdrawing the second probe and, entering in the joint space a third probe of substantially linear dimensions having a curve at a distal end, said curve terminating in a spatulate shape, and advancing said third probe and manipulating articular bone fragments to affect an anatomic reduction of the depression fracture in the joint space, and entering means for accessing the bone void into the access hole, charging said means with bone graft material and, selecting a fourth probe of substantially linear dimensions, terminating in a concave face perpendicular to a linear axis of said linear dimension, and advancing said bone graft material into any bone void created by manipulating bone fragments and reducing the fracture, and alternately advancing the third probe and manipulating articular bone fragments to affect an anatomic reduction of the depression fracture, and advancing further bone graft material into any bone void so as to affect percutaneously an anatomic reduction of the depression fracture.

\* \* \* \* \*